(12) United States Patent
Maznev

(10) Patent No.: US 6,587,794 B1
(45) Date of Patent: *Jul. 1, 2003

(54) METHOD FOR MEASURING THIN METAL FILMS

(75) Inventor: Alex Maznev, Natick, MA (US)

(73) Assignee: Koninklijke Philips Electronics N.V., Eindhoven (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/568,286

(22) Filed: May 10, 2000

Related U.S. Application Data

(60) Provisional application No. 60/146,398, filed on Jul. 30, 1999.

(51) Int. Cl.[7] .............................................. G06F 19/00
(52) U.S. Cl. ........................................ 702/28; 702/84
(58) Field of Search ................ 73/800, 597; 356/237.1, 356/318, 245, 345, 354, 357, 381, 432, 432 T, 496, 503, 630, 311; 438/7; 702/40, 170

(56) References Cited

U.S. PATENT DOCUMENTS

| | | | | |
|---|---|---|---|---|
| 4,952,061 A | * | 8/1990 | Edgar | 356/407 |
| 5,442,676 A | * | 8/1995 | Fewster | 378/72 |
| 5,490,728 A | * | 2/1996 | Schietinger et al. | 374/7 |
| 5,546,811 A | * | 8/1996 | Rogers et al. | 73/800 |
| 5,633,711 A | * | 5/1997 | Nelson et al. | 356/318 |
| 5,672,830 A | * | 9/1997 | Rogers et al. | 73/597 |
| 5,734,470 A | * | 3/1998 | Rogers et al. | 356/354 |
| 5,812,261 A | * | 9/1998 | Nelson et al. | 356/318 |
| 5,982,482 A | * | 11/1999 | Nelson et al. | 356/237.1 |
| 6,016,202 A | * | 1/2000 | Fuchs et al. | 356/432 T |
| 6,052,185 A | * | 4/2000 | Banet et al. | 356/345 |
| 6,069,703 A | * | 5/2000 | Banet et al. | 356/432 |
| 6,075,602 A | * | 6/2000 | Fuchs et al. | 356/357 |
| 6,081,330 A | * | 6/2000 | Nelson et al. | 356/318 |
| 6,118,533 A | * | 9/2000 | Banet et al. | 356/345 |
| 6,122,064 A | * | 9/2000 | Banet et al. | 356/381 |
| 6,174,739 B1 | * | 1/2001 | Steffan | 438/7 |
| 6,175,421 B1 | * | 1/2001 | Fuchs et al. | 356/503 |
| 6,188,478 B1 | * | 2/2001 | Fuchs et al. | 356/381 |
| 6,256,100 B1 | * | 7/2001 | Banet et al. | 356/432 |
| 6,348,967 B1 | * | 2/2002 | Nelson et al. | 356/432 |
| 6,366,861 B1 | * | 4/2002 | Waldhauer et al. | 702/35 |
| 6,393,915 B1 | * | 5/2002 | Banet et al. | 73/579 |

OTHER PUBLICATIONS

Gostein, M; Bailey, T C; Emesh, I; Diebold, A C; Maznev, A A; Banet, M; Sacco, R;"Thickness Measurement For Cu And Ta Thin Films Using Optoacoustics"; Proceedings of the IEEE 2000 International Conference on Interconnect Technology, 2000, pp. 176–178.*

Banet,M; Allen, L P; Nelson, K A; Fuchs, M; Rogers, J A; Akthukal, A ; Maznev A A;"Noncontact Acoustic Wave Metrology Of SOI Substrates"; Proceedings of the IEEE 1998 International Conference on SOI, 1998, pp. 45–46.*

(List continued on next page.)

Primary Examiner—John Barlow
Assistant Examiner—Douglas N Washburn

(57) ABSTRACT

A method and system for measuring properties of a sample are disclosed. At least one source of excitation radiation is used to irradiate the sample's surface. This excites multiple acoustic modes within the sample. A probe source of radiation diffracts off the acoustic modes to generate a signal beam. The signal beam is detected and analyzed to yields a signal waveform, from which a Fourier Transform spectrum is derived. The Fourier Transform spectrum features frequencies corresponding to the multiple acoustic modes. Analysis of the spectrum yields measurements of the sample's properties.

31 Claims, 6 Drawing Sheets

OTHER PUBLICATIONS

Banet, M; Fuchs, M; Logan, R A; Nelson, K A; Rogers, J A; "Noncontact Inspection Of Opaque Film Thickness In Single Layer And Multilayer Structures And Edge–Exclusion Zones"; IEEE 1997 Int'nl Symposium on Semiconductor Manufacturing Conf, 1997, pp. 35–37.*

Rogers, J A; Nelson, K A; "Photoacoustic Determination Of The Residual Stress And Transverse Elastic Moduli In Thin Films Of The Polyimide PMDA/ODA"; IEEE Transactions on Ultrasonics, Ferroelectrics and Frequency Control, vol. 4, Jul. 1995, pp. 555–556.*

"Thermal Conductivity"; American Institute Of Physics Handbook; Third Edition, 1972, pp. 4–142–4–148.*

* cited by examiner

METHOD FOR MEASURING THIN METAL FILMS

This application claims the benefit of Provisional Application No. 60/146,398 filed Jul. 30, 1999.

FIELD OF THE INVENTION

The present invention relates generally to the field of measurement methods and devices. More particularly, the present invention relates to the measurement of material properties using optically induced phonons.

BACKGROUND OF THE INVENTION

Due to a growing need to the semiconductor and other industries to accurately measure properties (e.g., thickness, composition) of structures such as thin films, Impulsive Stimulated Thermal Scattering (ISTS) arose as a useful measurement technique. ISTS is described, for example, in U.S. Pat. Nos. 5,633,711 (entitled MEASUREMENTS OF MATERIAL PROPERTIES WITH OPTICALLY INDUCED PHONONS); 5,546,811 (entitled OPTICAL MEASUREMENT OF STRESS IN THIN FILM SAMPLES); and 5,812,261 (entitled METHOD AND DEVICE FOR MEASURING THE THICKNESS OF OPAQUE AND TRANSPARENT FILMS), the contents of which are herein incorporated by reference.

In measurement systems using ISTS, a pair of laser pulses overlap on the surface of a structure to form an optical interference pattern. The structure absorbs the interference pattern to initiate a response, such as a sound wave (e.g., an acoustic mode), that propagates in a plane of the structure. A second laser pulse or beam diffracts off the acoustic mode to generate a signal beam whose amplitude is modulated. A detector detects the signal beam to generate a signal waveform, which is then sent to a processor that processes the signal waveform to generate a Fourier Transform spectrum that includes a spectral feature (e.g., a Gaussian or Lorentzian peak) that corresponds to a frequency of the fundamental acoustic mode. The frequency of the peak relates to a physical property (e.g., thickness) of the sample.

The accuracy to which the frequency can be measured depends on properties of the signal waveform, as well as other aspects of the reflected and diffracted probe beam. For example, the measured frequency of the fundamental peak in the Fourier Transform spectrum is especially sensitive to parasitically scattered light from the probe beam. This can result in errors in the frequency measured during ISTS, thereby affecting the performance (e.g., repeatability and reproducibility) of the measurement. In addition, measurement of just the fundamental peak only allows one property (e.g., a single thickness) to be measured at a time. This, of course, is a disadvantage, as semiconductor devices typically include multiple thin films, and in these samples it is usually desirable to simultaneously measure the thickness of more than one film, or thickness and another property of interest (e.g., resistivity).

There thus exists in the art a need for systems and methods that can improve the performance and repeatability of thickness measurements, as well as to simultaneously measure more than one property of the sample at a time.

BRIEF SUMMARY OF THE INVENTION

It is an object of the present invention to address the limitations of the conventional systems discussed above.

It is another object of the invention to provide improved methods and systems for measuring properties of samples, particularly those containing thin films and used in the semiconductor industry.

On aspect of the present invention is directed to an ISTS method that initiates, measures, and analyzes both the fundamental acoustic mode and higher-order acoustic modes of a sample under inspection.

Another aspect of the present invention relates to the ability to measure more than one property of a sample by measuring more than one mode of a Fourier transform spectrum simultaneously. Analysis of more than one mode can generate multiple property measurements simultaneously, for example, simultaneously measuring the thickness of two layers of a multilayer structure.

Another aspect of the invention relates to improved measurement repeatability resulting from measuring peaks corresponding to, e.g., a higher-order mode. Compared to the fundamental peak, this higher-order peak typically has a relatively narrow frequency bandwidth; it can therefore be measured with relative precision to improve properties such as measurement repeatability, reproducibility, and accuracy. In addition, the fundamental mode is affected adversely when light is scattered randomly off the surface of the sample. This light broadens the frequency bandwidth of the fundamental peak, thereby reducing the precision to which it can be measured. The frequency corresponding to a harmonic frequency (e.g., $2\omega_1$) is less sensitive to parasitically scattered light than the fundamental frequency (e.g., $\omega_1$) and can therefore be measured with better precision.

Yet another aspect of the invention relates to measuring a frequency component of the Fourier transform spectrum, and a decay constant of the time-domain waveform. The decay constant can be related to the resistivity of the measured film, and thus this measurement yields both a thickness and resistivity of the measured sample. In other embodiments the decay constant can be related to the thickness of a second film in the sample.

One preferred embodiment of the present invention is directed to a method for determining properties of a multi-layer structure. The method includes the steps of generating at least two excitation pulses, overlapping the two pulses to form an excitation pattern on or in the structure that modulates a probe beam to generate a signal beam, and detecting the modulation-induced signal beam. The signal includes at least two sub-component frequency values (e.g., a fundamental mode and a higher-order mode). The method also includes the step of analyzing the signal to determine at least two properties of the structure.

In a related embodiment, the signal includes a frequency component and a decay constant. The frequency component can be analyzed to determine a thickness of the structure, and the decay constant can be analyzed to determine a sructure's resistivity.

Another embodiment of the present invention is directed to an apparatus for determining a property of a structure. The apparatus includes at least one source of excitation radiation; a measurement system that forms an excitation pattern on or in the structure, using the excitation radiation, that causes a modulation response by at least a portion of the structure; and a detector that detects a signal based upon the modulation response. The signal includes at least one frequency value and at least one harmonic value of the frequency value. Alternatively, the signal is characterized by at least one frequency value and at least one decay constant. The apparatus also includes an analyzer that analyzes the harmonic value or decay constant to determine a property of the structure.

These and other embodiments and aspects of the present invention are exemplified in the following detailed disclosure.

BRIEF DESCRIPTION OF DRAWINGS

The features and advantages of the present invention can be understood by reference to the detailed description of the preferred embodiments set forth below taken with the drawings, in which.

DESCRIPTION OF THE PREFERRED EMBODIMENTS

Figure 1:
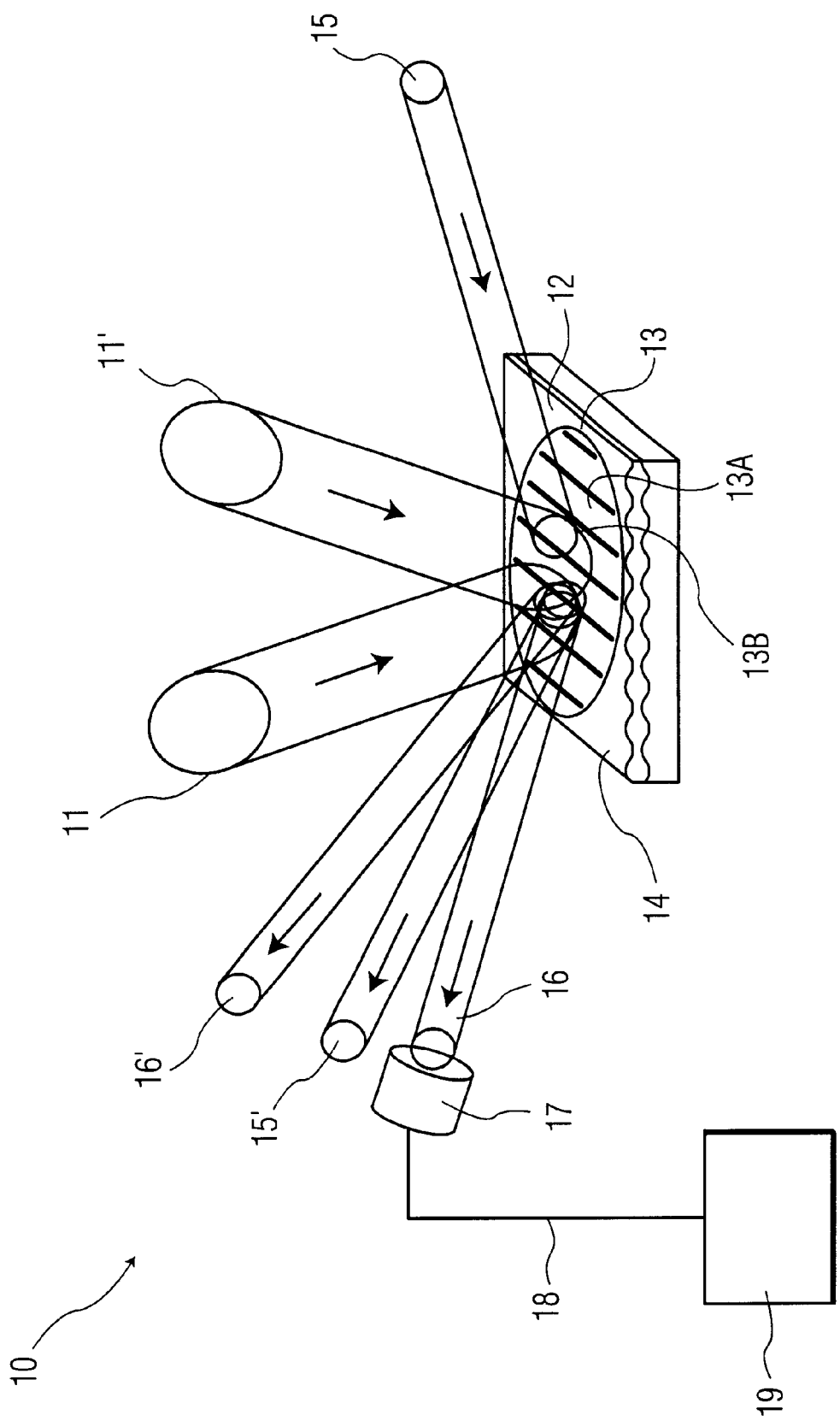
FIG. 1 is a schematic side view of a system for performing an ISTS measurement.
Figure 2A:
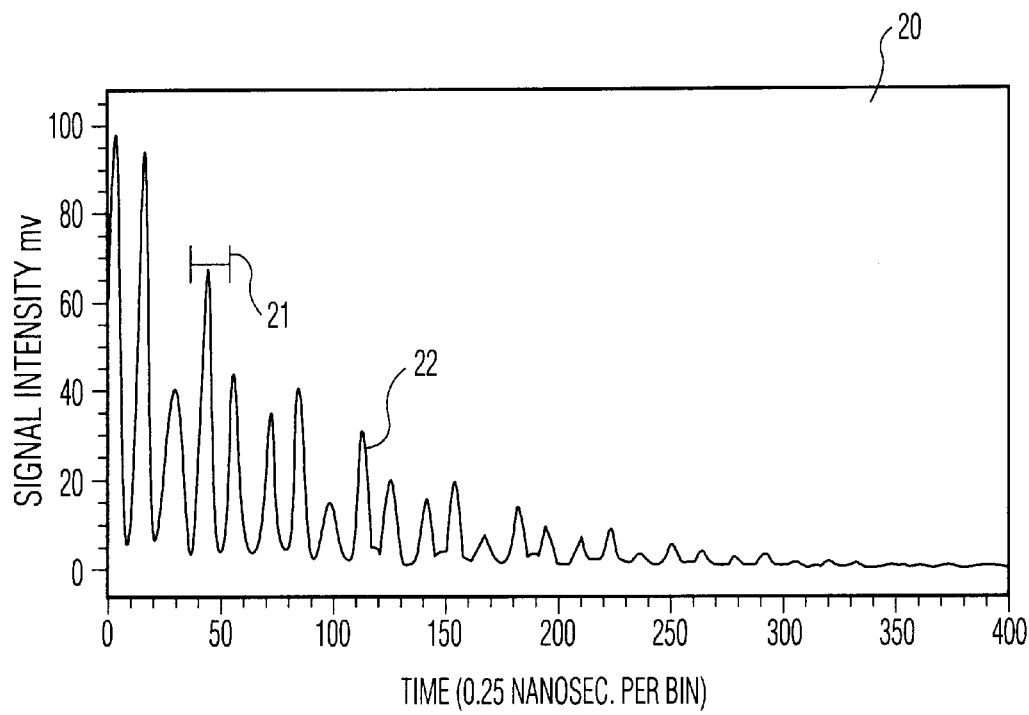
FIG. 2A is a graph of a time-domain signal waveform generated from more than one acoustic mode.
Figure 2B:
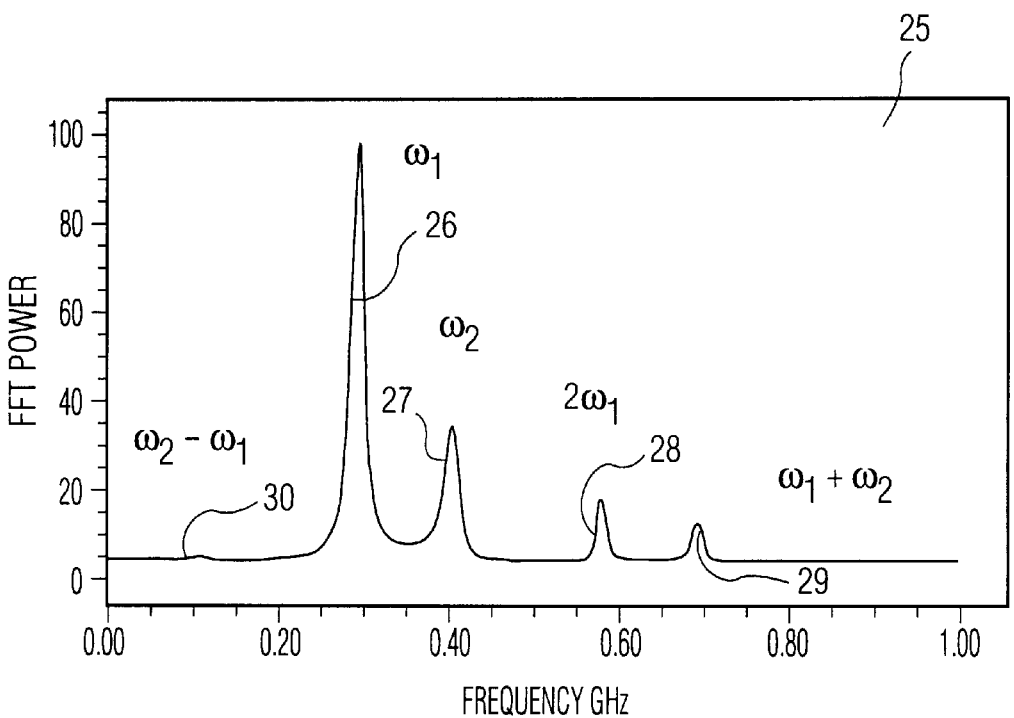
FIG. 2B is a graph of a Fourier Transform spectrum generated from the signal waveform of FIG. 2A characterized by peaks corresponding to several higher-order modes.

Referring to FIG. 1, a measurement system 10 (e.g., an ISTS measurement system) is shown. In the system 10 excitation pulses 11, 11' are overlapped on the surface of a sample 12 to form an excitation pattern 13 that contains alternating light 13A and dark 13B regions. When absorbed by the sample 12, the excitation pattern 13 launches multiple acoustic modes 14. The acoustic modes cause the surface of the sample 12 to ripple. A probe beam 15 then impinges sample 12 and reflects off the surface to form a reflected beam 15'. Portions of probe beam 15 diffract off the surface of sample 12 to form a pair of diffracted beams 16 and 16'. A photodetector 17 collects one or both of the diffracted beams 16 or 16' to generate an electrical signal 18 characterizing a signal waveform (as depicted in FIG. 2A). An analyzer 19 connected to the photodetector 17 receives the electrical signal 18 and processes it to generate a Fourier transform spectrum (as depicted in FIG. 2B). The processing, for example, can include taking a mathematical derivative of the signal waveform, and then taking a Fourier transform of the mathematical derivative.

Similar ISTS measurement systems and methods are described, for example, U.S. Pat. Nos. 5,633,711 (entitled MEASUREMENTS OF MATERIAL PROPERTIES WITH OPTICALLY INDUCED PHONONS); 5,546,811 (entitled OPTICAL MEASUREMENT OF STRESS IN THIN FILM SAMPLES); and 5,812,261 (entitled METHOD AND DEVICE FOR MEASURING THE THICKNESS OF OPAQUE AND TRANSPARENT FILMS), the contents of which have been previously incorporated by reference.

The analyzer 19 typically includes a processor/controller (e.g., a computer), a memory for storing data and an interface unit for receiving the electrical signal. The analyzer 19 may also include a network connection for interfacing to a data network, such as a variable-bandwidth network or the Internet, a display for displaying information to a user, a keyboard for inputting text and user commands, a mouse for positioning a cursor on the display and for inputting user commands, a disk drive for reading from and writing to floppy disks installed therein, and a CD-ROM drive for accessing information stored on CD-ROM.

In a preferred embodiment, the computations/operations performed by the analyzer 19 are implemented by computer-readable code executed by the analyzer 19. The code may be stored in a memory or read/downloaded from a memory medium such as a CD-ROM or floppy disk. In other embodiments, hardware circuitry may be used in place of, or in combination with, software instructions to implement the invention.

Referring to FIG. 2A, the signal waveform generated from the measurement system 10 in FIG. 1 is a time-domain signal waveform 20. The time-domain signal waveform 20 features oscillations 21 that correspond to the acoustic modes initiated in the sample by the excitation pattern. In some cases, multiple acoustic modes are simultaneously generated and then measured, resulting in a time-domain waveform characterized by a phenomenon called "signal beating". Signal beating occurs when more than one frequency is included in the time-domain signal waveform. This phenomenon generates additive and subtractive components, and accounts for the fluctuations of the peak amplitudes in time-domain signal waveform 20.

FIG. 2B is a Fourier transform 25 of the time-domain signal waveform 20 in FIG. 2A. The Fourier transform 25 depicts the different frequencies ($\omega_1$, $\omega_2$, $\omega_{1+2}$, $\omega_{1-2}$, $2\omega_1$) that are contained in the time-domain signal waveform 20 of FIG. 2A. The method for generating a Fourier transform spectrum from a time-domain signal waveform is well known in the art and not described herein in detail.

As shown in FIG. 2B, the Fourier transform spectrum 25 displays five peaks, each of which corresponds to a different frequency. Peaks 26 and 27 corresponds, respectively, to a fundamental acoustic mode (sometimes called a "Rayleigh" mode) of frequency $\omega_1$ and a second-order acoustic mode (sometimes called a "Sezawa" mode) of frequency $\omega_2$. Peak 29 corresponds to the sum of these two frequencies, i.e., $\omega_1+\omega_2$. Peak 30 corresponds to the difference between those two frequencies, i.e., $\omega_2-\omega_1$. Peak 28 represents the second harmonic of peak 26, i.e., $2\omega_1$.

It is known in the art to generate a single measurement of film thickness from the frequency corresponding to a fundamental acoustic mode, i.e., $\omega_1$. This method is described, for example, in U.S. Pat. No. 5,633,711 (entitled MEASUREMENT OF MATERIAL PROPERTIES WITH OPTICALLY INDUCED PHONONS).

It has been unexpectedly discovered that the thickness of two films in a multilayer sample can be determined by analyzing more than one acoustic mode, e.g., $\omega_1$ and $\omega_2$. Additionally, different peaks of the Fourier transform spectrum 25 can be used to improve upon convention, single-frequency measurements. For example, the frequency corresponding to the second harmonic peak 28 ($2\omega_1$) can be divided by a factor of two to find $\omega_1$. This operation has the unexpected functional advantage of producing sample measurements with a higher precision than by simply measuring the peak 26 corresponding to $\omega_1$. This is because the frequency $2\omega_1$ of peak 28 is less sensitive to parasitically scattered light than the frequency $\omega_1$ of peak 26.

It has also been unexpectedly discovered that, for some samples, a time constant describing the decay of the signal waveform relates to the resistivity of the outer film in the sample. Thus, for this measurement, a frequency (e.g., $\omega_1$) can be determined to measure the thickness of a film in the sample, and a decay constant can be determined to measure a resitivity of an outer film in the sample.

In a similar fashion, a single frequency (e.g., $\omega_1$) can be measured to determine the thickness of a total stack of films (e.g., both a copper and a tantalum film deposited on a silicon wafer). The decay constant can then be measured and related to just the copper film, thereby allowing the thickness of both films to be determined.

Referring again to FIG. 1, two crossed excitation beams 11 and 11' are used to initiate acoustic waves 14, which in turn can be measured to generate time-dependent signal waveforms (such as those depicted in FIG. 2A). One way to generate the crossed excitation beams 11, 11' is to pass a single excitation beam (not shown in the figure) through a pattern on an optical element called a "phase mask" (also not shown in the figure). The phase mask selectively diffracts the incident excitation beam into the two excitation beams 11, 11'. Phase masks are described in U.S. Pat. No. 5,734,470 (entitled DEVICE AND METHOD FOR TIME-RESOLVED OPTICAL MEASUREMENTS), the contents of which are incorporated by reference.

When the excitation beams 11, 11' are overlapped on the sample, they optically interfere to form a spatially and temporally varying excitation pattern 13 on the surface of the sample 12. The excitation pattern 13 contains light 13A and dark 13B regions that are spaced by a well-defined distance (typically between about 5 and 20 microns). The inverse of the spacing multiplied by a factor of $2\pi$ is the "wavevector" (typically indicated by the symbol "q") of the excitation pattern.

Translating the phase mask from one pattern to another adjusts the angle between the two excitation beams 11, 11'. This, in turn, adjusts the fringe spacing and the wavevector of the excitation pattern 13 on the surface of the sample 12. The acoustic frequency depends on the wavevector. Acoustic velocity (v) is defined as the frequency divided by the wavevector, and thus it too depends on the wavevector. Acoustic frequencies measured at multiple wavevectors is called the "dispersion" of the sample.

In a preferred embodiment, ISTS measurements like those described above are made at a single wavevector, and fundamental ($\omega_1$) and higher-order modes ($\omega_2$) are generated. The frequencies corresponding to these modes are determined by analyzing the Fourier transform spectrum. The thickness of two layers ($h_1$, $h_2$) in the sample is then determined using the linear equations:

$$v_1 = v_1(h_1, h_2) \tag{1}$$

$$v_2 = v_2(h_1, h_2) \tag{2}$$

where $v_1$ and $v_2$ are the acoustic velocities corresponding to the fundamental and higher-order modes.

Based on these equations, values for $h_1$, $h_2$ can be derived from an analytical model, such as that described in U.S. Pat. No. 5,812,261 (entitled METHOD AND DEVICE FOR MEASURING THE THICKNESS OF OPAQUE AND TRANSPARENT FILMS, the contents of which have been previously incorporated herein by reference) or can be determined empirically using calibration standards.

In another embodiment, $\omega_1$ and $\omega_2$ are measured at multiple wavevectors to generate dispersion curves of these two modes. The resulting dispersion curves can then be fit by the model functions:

$$v_1 = v_1(h_1, h_2, q) \tag{3}$$

$$v_2 = v_2(h_1, h_2, q) \tag{4}$$

to determine the values of $h_1$ and $h_2$.

Figure 3:
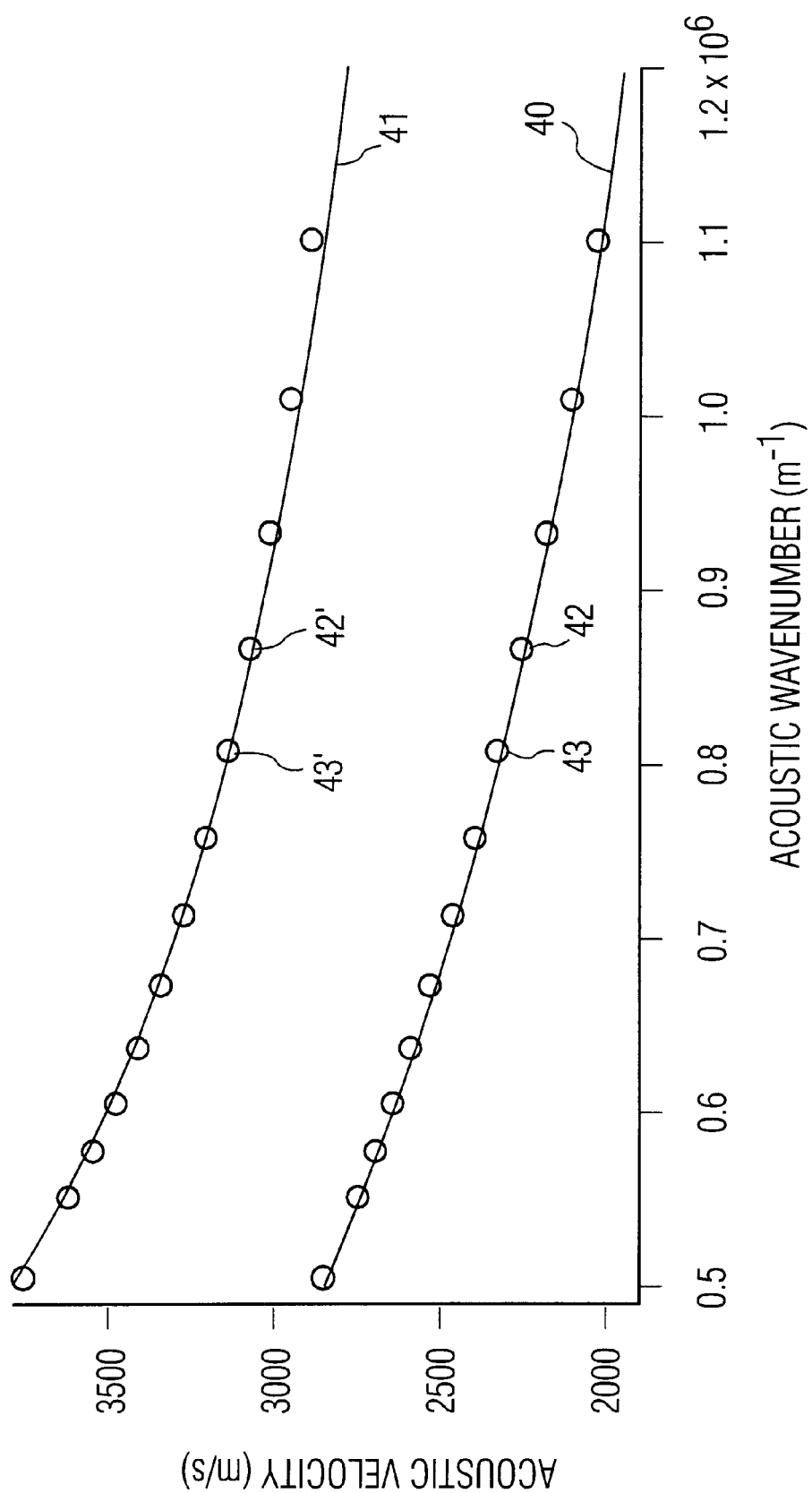
FIG. 3 is a chart of acoustic velocity (m/s) versus acoustic wavenumber ($m^{-1}$) for a multilayer sample.

As an example of this, FIG. 3 shows a pair of dispersion curves 40, 41 measured from a multilayer sample featuring tantalum/gold/oxide films deposited on an silicon wafer. Each dispersion curve shows a plot of acoustic velocity verses acoustic wavevector. The upper dispersion curve 41 corresponds to the dispersion of the higher-order mode $\omega_2$, while the lower dispersion curve 40 corresponds to the dispersion of the fundamental mode $\omega_1$. Each circle on the two curves corresponds to a measurement made at a different phase mask (corresponding to a different wavevector). For example, measurement points 42 and 43 represent two data points, generated using two separate phase masks, included in the lower dispersion curve 40 corresponding to $\omega_1$. Measurement points 42', 43' are included in the upper dispersion curve 41 corresponding to $\omega_2$. Both curves are fitted to the "best fit" dispersion curve (40 for $\omega_1$; 41 for $\omega_2$), shown as a solid line, that is described by a function shown in equations 3 and 4, above. The two thickness values of the sample are derived from the fitting function.

Figure 4A:
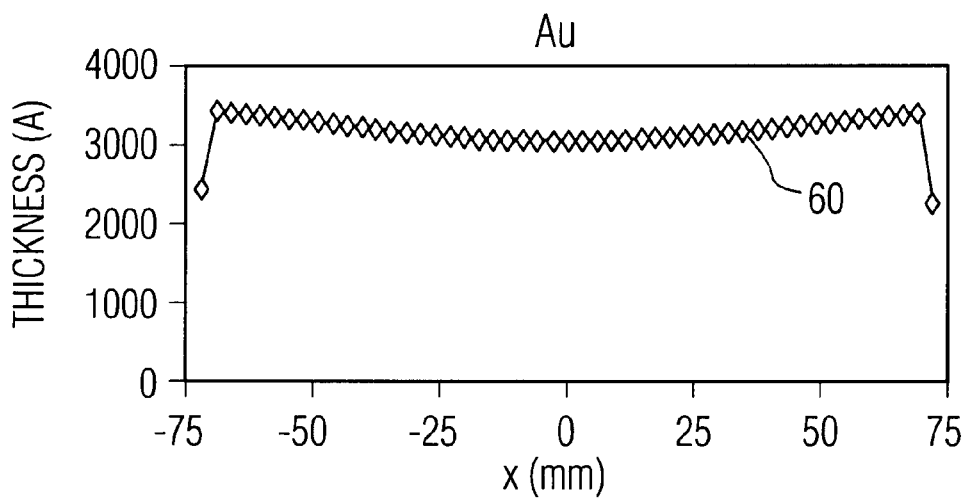
FIGS. 4A and 4B are graphs, respectively, of the thickness (Å) of gold and tantalum films contained in a multilayer sample measured across the sample's diameter (mm)
Figure 4B:
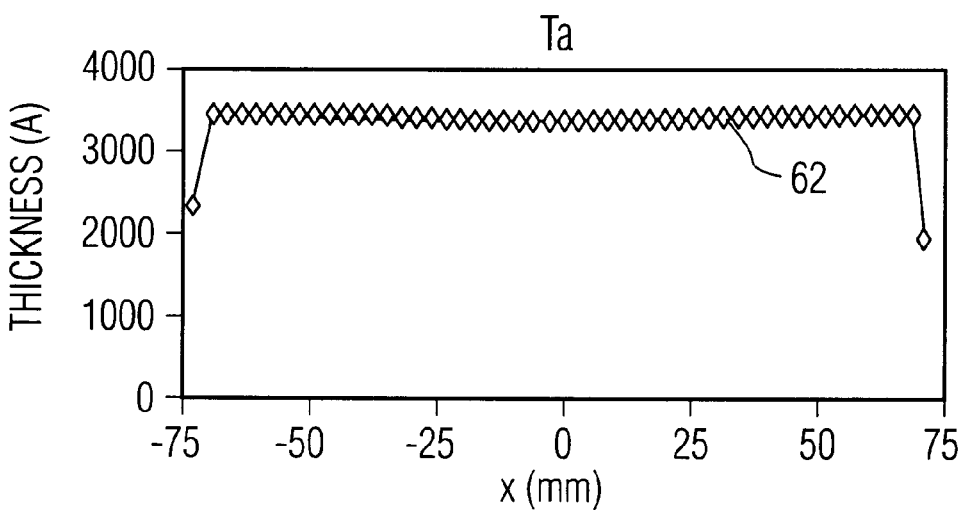

FIGS. 4A and 4B are plots that show data resulting from analysis of fundamental and higher-order modes measured at a single wavevector. The sample used for these measurements is the same as that used to generate the data for FIG. 3. The resulting data, in this case the thickness of both the gold (curve 60 in FIG. 4A) and tantalum (curve 62 in FIG. 4B) layers, are measured across the diameter of the sample. To generate the data points in FIGS. 4A and 4B, a measurement was made and the sample was translated; this process was repeated until measurements were made across the sample's diameter. As shown by the plots, the overlying gold film has a slight, inverted curvature, while the tantalum film is relatively flat.

Figure 5A:
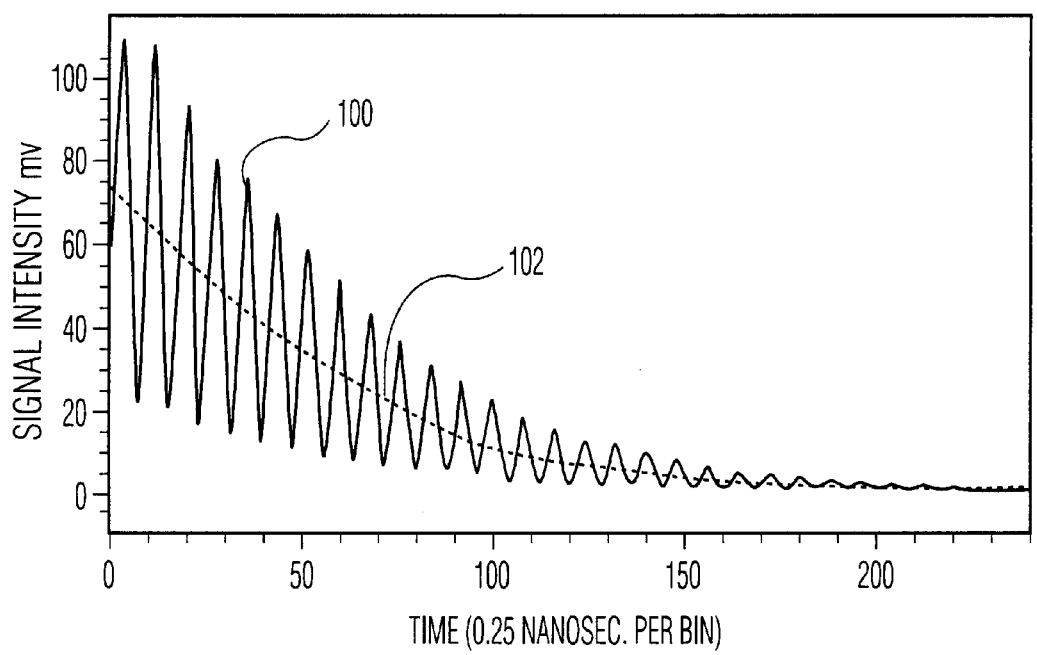
FIG. 5A is a graph of a time-domain signal waveform that is fit with an exponential decay function characterized by an exponential decay constant.
Figure 5B:
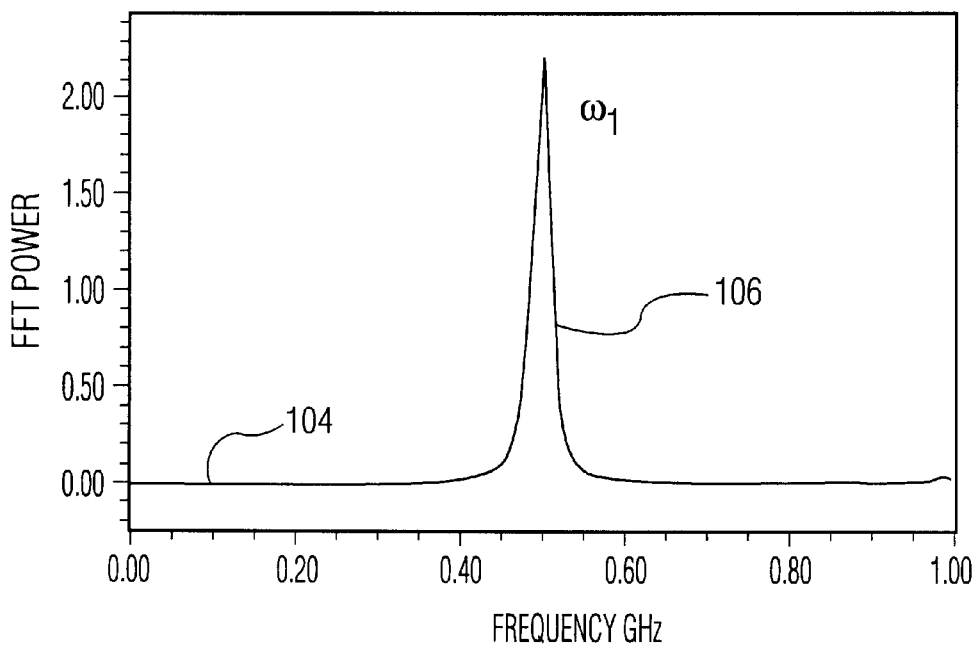
FIG. 5B is a graph of a Fourier Transform spectrum generated from the signal waveform of FIG. 5A.

In addition to higher-order modes, other properties of both the time-domain waveforms, such as decay time, can be analyzed to determine additional properties of the sample, such as electrical resistivity. To illustrate this point, FIGS. 5A and 5B show, respectively, a time-domain waveform 100 and the corresponding Fourier transform 104 measured from a copper/oxide/silicon structure. The time-domain waveform 100 has been fit with a dashed line 102 that represents the following mathematical function f(t):

$$f(t) = A\exp(-t/\gamma) \tag{5}$$

where A is the amplitude of the function, $\gamma$ is its decay time, and t represents the variable for time.

It can be shown that for some samples (e.g., those containing copper films) measured with ISTS, like that described above, the decay time $\gamma$ is related to the electrical resistivity of the copper film. In this model, the outer metal film (typically 1000 Å to 1 micron) is assumed to be very thin compared to the acoustic wavelength (typically 5–20 microns), and the thermal conductivity of the oxide can be disregarded. In this case, only the lateral heat transport in the metal film is relevant. For this model, the decay time $\gamma$ of the ISTS signal is given by $$\gamma \sim 1/(2\ q^2 \tau) \tag{6}$$

where $\tau$ is the thermal conductivity of the metal and q is the acoustic wavevector. In good electrical conductors such as copper, the ratio of the thermal conductivity to electrical conductivity σ at a given temperature T is a material-independent constant (this is sometimes called the Wiedemann-Franz law):

$$\tau/\sigma = LT \qquad (7)$$

where L is a constant called Lorentz number. Thus, for copper, the signal decay time can be expected to be approximately proportional to the electrical resistivity:

$$\gamma \sim 1/(2\ q^2 \sigma L T) \qquad (8)$$

Figure 6:
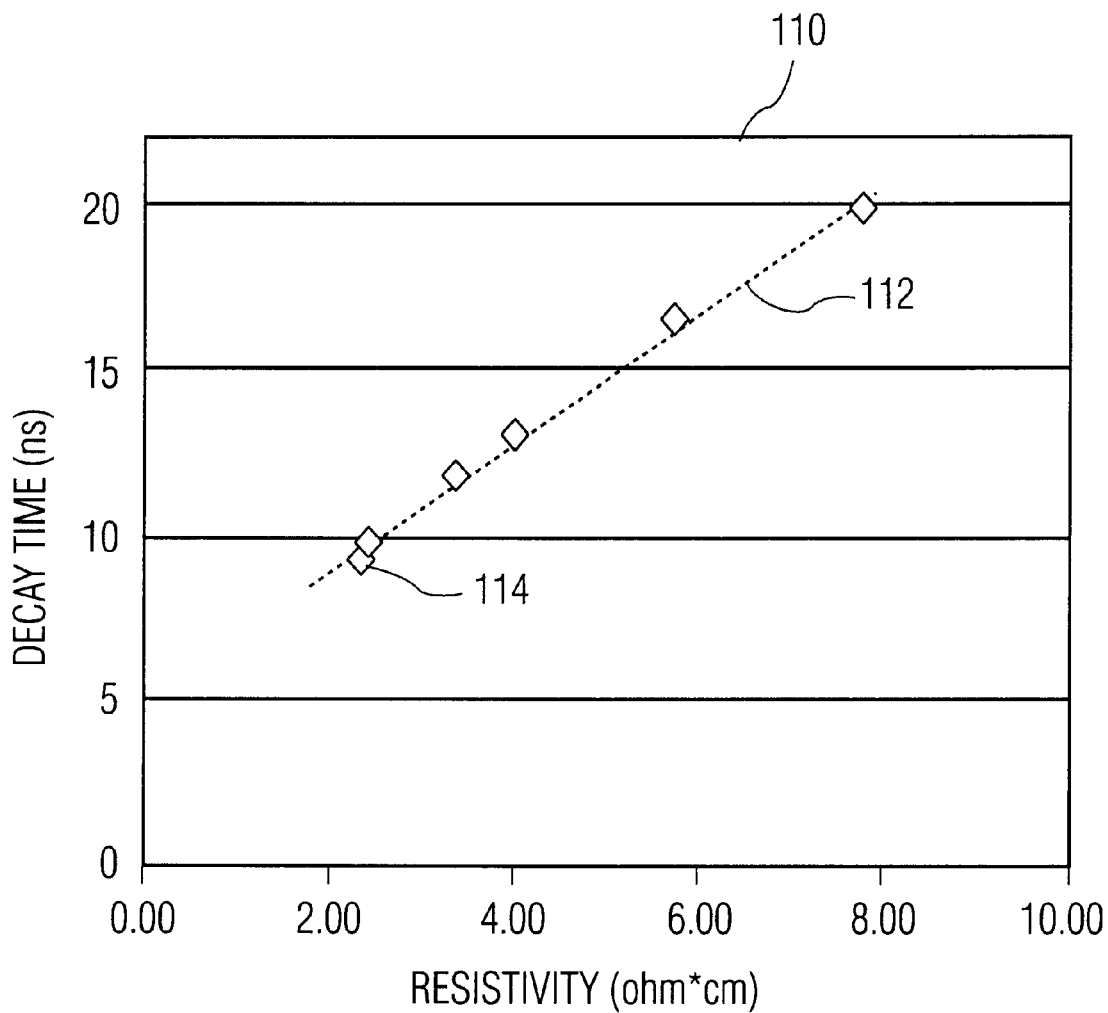
FIG. 6 is a graph of the exponential decay constant (ns) similar to that used to fit the data of FIG. 5A versus electrical resistivity (ohm*cm) as measured from a set of copper/oxide/silicon samples.

Equations 6–8 are verified by the data shown in FIG. 6. Here, a set (6 samples) of copper/oxide/silicon structure, each having an outer film of copper with a different thickness and a constant oxide thickness, were measured using ISTS to determine the decay constant (in units of ns). The same films were also measured with a combination of a 4-point probe (which measures sheet resistivity in units of Ω per area) and Grazing Incidence X-ray reflection (which measures absolute thickness). The resistivity (in units of Ω*cm) of the copper films was determined by multiplying the film thickness by the sheet resistivity. The decay time measured from the copper films using ISTS was then plotted as a function of the resistivity.

The data plotted in FIG. 6 clearly indicates that the decay time increases in a nearly linear fashion with the electrical resistivity. In this plot, data points 114 correspond to each of the 6 samples. A dashed line 112 is drawn through the data to indicate the linear dependence of the data.

To make an actual measurement, data like that shown in the figure can be stored in a "look-up" table; when an actual measurement is made, the decay time g can be determined by fitting the signal waveform to a function similar to that shown in equation 5. This value can then be compared to the look-up table to determine electrical resistivity. Alternatively, the relationship between decay time and resistivity could be represented by a mathematical function coded into a computer program. Once determined, the decay constant could be input to the computer program to determine the resistivity. In both cases, this means that in a single measurement the film thickness can be determined by analyzing the acoustic frequency, and the resistivity can be determined by analyzing the decay time.

Similar measurements of thickness and resistivity can be made on patterned copper "Damascene" features, as described in pending U.S. Patent Application Ser. No. 09/067,411 (entitled METHOD AND DEVICE FOR MEASURING THE THICKNESS OF THIN FILMS NEAR A SAMPLES'S EDGE AND IN A DAMASCENE-TYPE STRUCTURE), the contents of which are incorporated herein by reference.

While the present invention has been described above in terms of specific embodiments, it is to be understood that the invention is not intended to be confined or limited to the embodiments disclosed herein. On the contrary, the present invention is intended to cover various methods, structures and modifications thereof included within the spirit and scope of the appended claims.

What is claimed is:

1. A method for determining properties of a multilayer structure, comprising the steps of:
   generating at least two excitation pulses:
   forming an excitation pattern on or in the structure, using the two excitation pulses, that causes a modulation response by at least a portion of the structure;
   detecting a signal based upon the modulation response, the signal including at least two sub-component frequency values; and
   analyzing the at least two sub-component frequency values of the signal to determine at least two properties of the structure by analyzing one of (1) more than one acoustic mode of the signal and (2) a time constant indicating decay of the signal.

2. The method according to claim 1, wherein the at least two properties are determined essentially simultaneously.

3. The method according to claim 1, wherein the at least two properties are respective thickness values of respective layers of the structure.

4. The method according to claim 3, wherein said analyzing step includes analyzing the at least two sub-component frequency values of the signal to determine acoustic mode values and/or elements of a Fourier transform spectrum.

5. The method according to claim 4, wherein said analyzing step further includes generating at least two dispersion curves in accordance with the at least two sub-component frequency values, the respective thickness values being determined in accordance with the at least two dispersion curves.

6. The method according to claim 5, wherein the at least two dispersion curves are analyzed simultaneously to determine the respective thickness values.

7. The method according to claim 1, wherein the signal is generated using the Impulse Stimulated Thermal Scattering (ISTS) technique.

8. A method for determining a property of a structure, comprising the steps of:
   generating at least two excitation pulses;
   forming an excitation pattern on or in the structure, using the two excitation pulses, that causes a modulation response by at least a portion of the structure;
   detecting a signal based upon the modulation response, the signal including at least one frequency value and at least one harmonic value of the at least one frequency value; and
   measuring the at least one harmonic value of said at least one frequency value to the determine the property of the structure.

9. The method according to claim 8, wherein the property is a thickness value of the structure.

10. The method according to claim 9, wherein the one frequency value is a fundamental mode value and the one harmonic value is a second or higher-order harmonic value of the fundamental mode value.

11. The method according to claim 10, wherein the fundamental mode value is based upon an acoustic mode value of the signal.

12. The method according to claim 8, wherein the signal is generated using Impulse Stimulated Thermal Scattering (ISTS) techniques.

13. An apparatus for determining properties of a multilayer structure, comprising:
   at least one source of excitation radiation;
   a measurement system capable of forming an excitation pattern on or in the structure, using the excitation radiation, that causes a modulation response by at least a portion of the structure;
   a detector, coupled to the measurement system, capable of detecting a signal based upon the modulation response, the signal including at least two sub-component frequency values; and
   an analyzer, coupled to the detector, capable of determining at least two properties of the structure in accordance with the respective at least two sub-component frequency values of the signal.

14. The apparatus according to claim 13, wherein the at least two properties are determined essentially simultaneously.

15. The apparatus according to claim 13, wherein the at least two properties are respective thickness values of respective layers of the structure.

16. The apparatus according to claim 15, wherein said analyzer is capable of analyzing independently the at least two sub-components of the signal.

17. The apparatus according to claim 16, wherein the sub-components of the signal comprise acoustic mode values, frequency values and/or elements of a Fourier transform spectrum.

18. The apparatus according to claim 16, wherein said analyzer is further capable of generating at least two dispersion curves in accordance with the at least two sub-components, the respective thickness values being determined in accordance with the at least two dispersion curves.

19. An apparatus for determining a property of a structure, comprising:

at least one source of excitation radiation;

a measurement system capable of forming an excitation pattern on or in the structure, using the excitation radiation, that causes a modulation response by at least a portion of the structure;

a detector, coupled to the measurement system, capable of detecting a signal based upon the modulation response, the signal including at least one frequency value and at least one harmonic value of the one frequency value; and an analyzer coupled to the detector, capable of measuring the at least one harmonic value to determine the property of the structure.

20. The apparatus according to claim 19, wherein the property is a thickness value of the structure.

21. The apparatus according to claim 19, wherein the at least one frequency value is a fundamental mode value and the at least one harmonic value is a second or higher order harmonic value of the fundamental mode value.

22. The apparatus according to claim 21, wherein the fundamental mode value is based upon an acoustic mode value of the signal.

23. A memory medium including code for controlling, when executed, an analyzer for an apparatus for determining at least two properties of a multilayer structure, the code comprising:

code for receiving a signal based upon a modulation response by at least a portion of the structure caused by an excitation pattern on or in the structure, the signal including at least two sub-component frequency values; and code for determining at least two properties of the structure in accordance with the signal.

24. A memory medium including code for controlling, when executed, an analyzer for an apparatus for determining at least one property of a structure, the code comprising:

code for receiving a signal based upon a modulation response by at least a portion of the structure caused by an excitation pattern on or in the structure, the signal including at least one frequency value and at least one harmonic value of the at least one frequency value; and code for analyzing a measurement of the at least one harmonic value to determine the property of the structure.

25. A method for determining an electrical resistivity of a film in a sample, comprising the steps of:

irradiating the sample with at least one optical excitation pulse to generate a response characterized by an acoustic wave and a decaying component;

irradiating the sample with an optical probe beam to generate a probe beam that is modulated by the acoustic wave and decaying component;

detecting the probe beam to generate an electrical signal waveform;

analyzing the electrical signal waveform to characterize the acoustic wave and the decaying component; and determining the electrical resistivity by analyzing the decaying component.

26. The method of claim 25, wherein the analyzing step further comprises comparing the electrical signal waveform to a mathematical function.

27. The method of claim 26, wherein the mathematical function comprises an exponential function.

28. The method of claim 25, wherein the determining step further comprises comparing the decaying component to a mathematical model that relates the decaying component to electrical resistivity.

29. The method of claim 28, wherein the mathematical function is a look-up table or a linear function.

30. The method of claim 25, wherein the decaying component corresponds to a thermal process.

31. A method for determining the thickness of two films in a sample, comprising the steps of:

irradiating the sample with at least one optical excitation pulse to generate a response characterized by an acoustic wave component and a decaying component;

irradiating the sample with an optical probe beam to generate a probe beam that is modulated by the acoustic wave and decaying components;

detecting the probe beam to generate an electrical signal waveform;

analyzing the electrical signal waveform to characterize the acoustic wave and the decaying components;

determining the thickness of at least one film by analyzing the acoustic wave component;

and determining the thickness of at least one film by analyzing the decaying component, wherein the analyzing step further comprises comparing the electrical signal waveform to a mathematical function and the mathematical function comprises an exponential function.

* * * * *